United States Patent
Kandeel

(10) Patent No.: US 11,801,249 B1
(45) Date of Patent: Oct. 31, 2023

(54) BROAD-SPECTRUM ANTITRYPANOSOMAL COMPOUNDS

(71) Applicant: KING FAISAL UNIVERSITY, Al-Ahsa (SA)

(72) Inventor: Mahmoud Kandeel, Al-Ahsa (SA)

(73) Assignee: KING FAISAL UNIVERSITY, Al-Ahsa (SA)

( * ) Notice: Subject to any disclaimer, the term of this patent is extended or adjusted under 35 U.S.C. 154(b) by 0 days.

(21) Appl. No.: 18/130,412

(22) Filed: Apr. 3, 2023

(51) Int. Cl.
*A61K 31/52* (2006.01)

(52) U.S. Cl.
CPC .................................. *A61K 31/52* (2013.01)

(58) Field of Classification Search
CPC ...................................................... A61K 31/52
See application file for complete search history.

(56) References Cited

PUBLICATIONS

Meier et al. Frontiers in Chemistry, Mar. 2018, vol. 6, Article 88, 23 pages (Year: 2018).*

Aguilera et al. Pharmaceuticals, 2023, vol. 16, No. 20, 23 pages (Year: 2023).*
PubChem, "4-[3-[4-(4-fluorophenyl)-1H-pyrazol-5-yl]piperidin-1-yl]-7H-pyrrolo[2,3-d]pyrimidine", CID 56742906 (2012).
PubChem, "6-{3-[4-(4-fluorophenyl)-1H-pyrazol-5-yl]piperidin-1-yl}-9H-purine", CID 76408947 (2014).
PubChem, "6-[3-[4-(4-fluorophenyl)-1H-pyrazol-5-yl]piperidin-1-yl]-7H-purine", CID 56757235 (2012).
PubChem, "6-[4-[4-(3-fluorophenyl)-1H-pyrazol-5-yl]piperidin-1-yl]-7H-purine", CID 56758337 (2012).
PubChem, "6-[4-(3-phenyl-1H-1,2,4-triazol-5-yl)piperidin-1-yl]-7H-purine", CID 75371370 (2014).

* cited by examiner

*Primary Examiner* — James D. Anderson
(74) *Attorney, Agent, or Firm* — Nath, Goldberg & Meyer; Richard C. Litman

(57) ABSTRACT

A method of treating a protozoan infection includes administering an antiprotozoal agent to a patient in need thereof. The antiprotozoal agent is selected from Compound 1 (4-{3-[4-(4-fluorophenyl)-1H-pyrazol-5-yl]piperidin-1-yl}-7H-pyrrolo[2,3-d]pyrimidine) and Compound 2 (6-{3-[4-(4-fluorophenyl)-1H-pyrazol-5-yl]piperidin-1-yl}-9H-purine). Compounds 1 and 2 exhibit broad spectrum trypanocidal activity.

6 Claims, No Drawings

BROAD-SPECTRUM ANTITRYPANOSOMAL COMPOUNDS

BACKGROUND

1. Field

The disclosure of the present patent application relates to novel compounds that have trypanocidal activity.

2. Description of the Related Art

Parasitic protozoan infections are a major concern for human health. The genus *Trypanosoma* includes several species known to cause parasitic infection in both humans and animals, including, among others, *Trypanosoma brucei rhodesiense* and *Trypanosoma brucei gambiense*, implicated as the cause of Human African Trypanosomiasis (HAT, or African sleeping sickness); *Trypanosoma evansi*, causing Surra, which is rapidly fatal in camels and horses; *Trypanosoma congolense*, causing cerebral trypanosomiasis in animals; *Trypanosoma cruzi*, causing Chagas disease (American trypanosomiasis, or South American sleeping sickness); etc.

In addition to the cost of human suffering many of the animals afflicted with trypanosomiasis are important for both domestic use and commercially.

Research has suggested that some species of *Trypanosoma* have developed mechanisms for avoiding attack by the human immune system. Therefore, the development of pharmaceuticals and chemotherapy for treating and controlling parasitic infections by *Trypanosoma* organisms is deemed very important. Nevertheless, development of such pharmaceuticals is still in its early stages, and the pharmaceuticals currently available are often found to be less than fully effective. Thus, broad-spectrum antitrypanosomal compounds solving the aforementioned problems are desired.

SUMMARY

In an embodiment, the present subject matter relates to a method of treating a protozoan infection in a patient, comprising administering to a patient in need thereof a therapeutically effective amount of a pharmaceutical composition comprising an antiprotozoal compound and a pharmaceutically acceptable carrier, the antiprotozoal compound being selected from the group consisting of:

4-{3-[4-(4-fluorophenyl)-1H-pyrazol-5-yl]piperidin-1-yl}-7H-pyrrolo[2,3-d]pyrimidine having the formula:

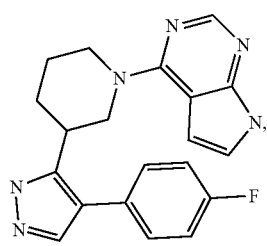

6-{3-[4-(4-fluorophenyl)-1H-pyrazol-5-yl]piperidin-1-yl}-9H-purine having the formula:

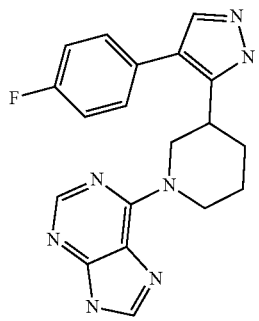

and a pharmaceutically acceptable salt, ester stereoisomer, or solvate thereof.

These and other features of the methods of treating a protozoan infection will become readily apparent upon further review of the following specification.

DETAILED DESCRIPTION OF THE EMBODIMENTS

The following definitions are provided for the purpose of understanding the present subject matter and for construing the appended patent claims.

Throughout the application, where compositions are described as having, including, or comprising specific components, or where processes are described as having, including, or comprising specific process steps, it is contemplated that compositions of the present teachings can also consist essentially of, or consist of, the recited components, and that the processes of the present teachings can also consist essentially of, or consist of, the recited process steps.

It is noted that, as used in this specification and the appended claims, the singular forms "a" "an", and "the" include plural references unless the context clearly dictates otherwise.

In the application, where an element or component is said to be included in and/or selected from a list of recited elements or components, it should be understood that the element or component can be any one of the recited elements or components, or the element or component can be selected from a group consisting of two or more of the recited elements or components. Further, it should be understood that elements and/or features of a composition or a method described herein can be combined in a variety of ways without departing from the spirit and scope of the present teachings, whether explicit or implicit herein.

The use of the terms "include," "includes", "including," "have," "has," or "having" should be generally understood as open-ended and non-limiting unless specifically stated otherwise.

The use of the singular herein includes the plural (and vice versa) unless specifically stated otherwise. In addition, where the use of the term "about" is before a quantitative value, the present teachings also include the specific quantitative value itself, unless specifically stated otherwise. As used herein, the term "about" refers to a ±10% variation from the nominal value unless otherwise indicated or inferred.

The term "optional" or "optionally" means that the subsequently described event or circumstance may or may not occur, and that the description includes instances where said event or circumstance occurs and instances in which it does not.

The term "isomers" or "stereoisomers" as used herein relates to compounds that have identical molecular formulae but that differ in the arrangement of their atoms in space. Stereoisomers that are not mirror images of one another are termed "diastereoisomers" and stereoisomers that are non-superimposable mirror images are termed "enantiomers," or sometimes optical isomers. A carbon atom bonded to four non-identical substituents is termed a "chiral center." Certain compounds herein have one or more chiral centers and therefore may exist as either individual stereoisomers or as a mixture of stereoisomers. Configurations of stereoisomers that owe their existence to hindered rotation about double bonds are differentiated by their prefixes cis and trans (or Z and E), which indicate that the groups are on the same side (cis or Z) or on opposite sides (trans or E) of the double bond in the molecule according to the Cahn-Ingold-Prelog rules. All possible stereoisomers are contemplated herein as individual stereoisomers or as a mixture of stereoisomers.

Unless defined otherwise, all technical and scientific terms used herein have the same meaning as commonly understood to one of ordinary skill in the art to which the presently described subject matter pertains.

Where a range of values is provided, for example, concentration ranges, percentage ranges, or ratio ranges, it is understood that each intervening value, to the tenth of the unit of the lower limit, unless the context clearly dictates otherwise, between the upper and lower limit of that range and any other stated or intervening value in that stated range, is encompassed within the described subject matter. The upper and lower limits of these smaller ranges may independently be included in the smaller ranges, and such embodiments are also encompassed within the described subject matter, subject to any specifically excluded limit in the stated range. Where the stated range includes one or both of the limits, ranges excluding either or both of those included limits are also included in the described subject matter.

Throughout the application, descriptions of various embodiments use "comprising" language. However, it will be understood by one of skill in the art, that in some specific instances, an embodiment can alternatively be described using the language "consisting essentially of" or "consisting of".

"Subject" as used herein refers to any animal classified as a mammal, including humans, domestic and farm animals, and zoo, sports, and pet companion animals such as household pets and other domesticated animals such as, but not limited to, cattle, sheep, ferrets, swine, horses, poultry, rabbits, goats, dogs, cats and the like.

"Patient" as used herein refers to a subject in need of treatment of a condition, disorder, or disease, such as an acute or chronic airway disorder or disease.

For purposes of better understanding the present teachings and in no way limiting the scope of the teachings, unless otherwise indicated, all numbers expressing quantities, percentages or proportions, and other numerical values used in the specification and claims, are to be understood as being modified in all instances by the term "about". Accordingly, unless indicated to the contrary, the numerical parameters set forth in the following specification and attached claims are approximations that may vary depending upon the desired properties sought to be obtained. At the very least, each numerical parameter should at least be construed in light of the number of reported significant digits and by applying ordinary rounding techniques.

In an embodiment, the present subject matter relates to a method of treating a protozoan infection in a patient, comprising administering to a patient in need thereof a therapeutically effective amount of a pharmaceutical composition comprising an antiprotozoal compound and a pharmaceutically acceptable carrier, the antiprotozoal compound being selected from the group consisting of:

Compound 1: 4-{3-[4-(4-fluorophenyl)-1H-pyrazol-5-yl]piperidin-1-yl}-7H-pyrrolo[2,3-d]pyrimidine having the formula:

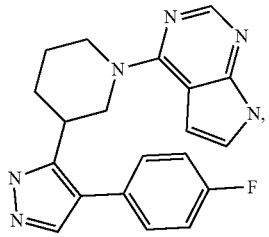

Compound 2: 6-{3-[4-(4-fluorophenyl)-1H-pyrazol-5-yl]piperidin-1-yl}-9H-purine having the formula:

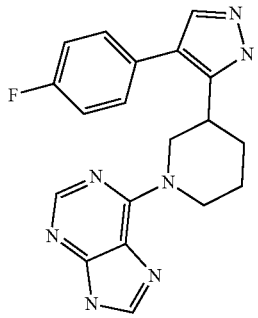 [SMILES: Fc1ccc(-c2cn[nH]c2C2CCCN(c3ncnc4[nH]cnc34)C2)cc1]

and a pharmaceutically acceptable salt, ester stereoisomer, or solvate thereof.

In one embodiment, the protozoan treatable with the present compounds is of a *Trypanosoma* genus. In this regard, the protozoan can be selected from the group consisting of *T. brucei, T. evansi, T. equiperdum*, and *T. congolense*. Further in this regard, the protozoan can be selected from the group consisting of *Trypanosoma brucei brucei* GUTat3.1, *T. b. rhodesiense* IL1501, *T. b. gambiense* IL1922, *T. evansi* Tansui, *T. equiperdum* IVM-t1, and *T. congolense* IL3000.

In an embodiment, the method can include administering a pharmaceutical composition including the inhibitory compound and a pharmaceutically acceptable carrier. The phrase "pharmaceutically acceptable," as used herein, refers to molecular entities and compositions that do not produce an allergic or similar untoward reaction when administered to a human. As used herein, a "carrier" includes any and all solvents, dispersion media, vehicles, coatings, diluents, isotonic and absorption delaying agents, buffers, carrier solutions, suspensions, colloids, excipients, and the like. A therapeutically effective amount of the compound or an amount effective to treat inflammation may be determined initially from the Examples described herein and adjusted for specific targeted diseases using routine methods. The present compositions can be in unit dosage forms such as tablets, pills, capsules, powders, granules, ointments, sterile parenteral solutions or suspensions, metered aerosol or liquid sprays, drops, ampules, auto-injector devices or suppositories, for oral parenteral, intranasal, sublingual or rectal administration, or for administration by inhalation or insufflation. The composition can be presented in a form suitable for daily, weekly, or monthly administration. The pharmaceutical compositions herein will contain, per dosage unit, e.g., tablet, capsule, powder, injection, teaspoonful, suppository and the like, an amount of the active ingredient necessary to deliver an effective dose.

Accordingly, in an embodiment, the antiprotozoal compound can be administered orally to the patient.

As described in detail below, an initial virtual screening of numerous compounds was conducted to identify candidate compounds having sufficient binding potency with *Trypanosoma brucei* dihydroorotate dehydrogenase, which is an important antimicrobial and antiprotozoal target. Further assessment of the candidates identified by the virtual screening was then conducted based on computational phaxnacokinetic features, drug-likeness, percent of oral absorption in humans, anticipated carcinogenicity, mutagenicity, and toxicity testing. After virtual screening, two compounds were chosen for further in vitro assessment for their trypanocidal activity based on their high binding scores, as the two compounds showed strong binding with docking score exceeding −10.00, which implies strong binding interaction with *Trypanosoma brucei* dihydroorotate dehydrogenase.

Compound 1 (4-{3-[4-(4-fluorophenyl)-1H-pyrazol-5-yl]piperidin-1-yl}-7H-pyrrolo[2,3-d]pyrimidine) and Compound 2 (6-{3-[4-(4-fluorophenyl)-1H-pyrazol-5-yl]piperidin-1-yl}-9H-purine) each proved to be excellent candidates for use as antitrypanosomal agents.

Table 1 identifies the formal chemical name and source for each of Compounds 1-2.

TABLE 1

Chemical Names for Compounds 1 and 2

| Compound | Chemical name | Vendor | ID |
| --- | --- | --- | --- |
| Compound 1 | 4-{3-[4-(4-fluorophenyl)-1H-pyrazol-5-yl]piperidin-1-yl}-7H-pyrrolo[2,3-d]pyrimidine | Chembridge Corporation (San Diego, CA, USA) | Compound 1 29099410 |
| Compound 2 | 6-{3-[4-(4-fluorophenyl)-1H-pyrazol-5-yl]piperidin-1-yl}-9H-purine | Chembridge Corporation (San Diego, CA, USA) | Compound 2 86450659 |

The present teachings are illustrated by the following examples.

Example 1

Materials and Methods

The Schrodinger Maestro molecular modeling package (Schrodinger LLC, New York, USA) was used in all virtual screening modeling steps. QikProp software tools are an accurate, rapid, and simple-to-use method for predicting molecular properties. The QikProp software application compares the properties of a specified molecule with the properties of compounds found in 95 percent of commonly prescribed medications. To find any probable places between the active-site space of the receptor and the ligand, a gradable sequence of filters is used to attempt to locate them. A grid composed of different sets of fields that eventually give various correct gradings of the ligand poses while also justifying and representing the structure and features of the receptor is created. The compounds' 2D structures were processed by Ligprep, and finally, 3D optimized at the physiologic pH.

Example 2

Molecular Docking

Docking runs were performed to check the binding potency with *Trypanosoma brucei* dihydroorotate dehydrogenase, which is an important antimicrobial and antiprotozoal target. Minimal changes were made to the protocols for protein expression, ligand design, and docking that were previously described in Burayk et al. (2022): "Drug Discovery of New Anti-Inflammatory Compounds by Targeting Cyclooxygenases", *Pharmaceuticals* 15, 282; and Kandeel et al. (2021): "Virtual Screening and Inhibition of Middle East Respiratory Syndrome Coronavirus Replication by Targeting Papain-like Protease" *Dr. Sulainan Al Habib Medical Journal* 3, 179-187.

Using the protein preparation module, the docking of the PDB 3RG9 structure was optimized. Detrimental crystallographic chemicals and surplus water molecules were removed from the solution. The protein was made protonated by the addition of polar hydrogens, and the OPLS2005 force field was used to optimize the structures and reduce the overall energy. For docking grid generation, WR99210 was employed as the center of a 20 Å grid box.

The Standard SP Glide docking approach was applied, and docking scores were used to rank the final findings. For verification, WR99210 was redocked, and when compared to the bound ligand, the docking position was found to be fully complementary and had a small root-mean-squared deviation (RMSD).

After virtual screening the two compounds identified herein were selected after showing favorably high binding scores. The two compounds showed strong binding with docking score exceeding −10.00, which implies strong binding interaction with *Trypanosoma brucei* dihydroorotate dehydrogenase (Table 2).

TABLE 2

The docking score and binding parameters for compounds 1 and 2 with *Trypanosoma brucei* dihydroorotate dehydrogenase.

| compound | Name | Docking Score (kcal/mol) | Glide Hbond | Glide Lipo | Glide Evdw |
| --- | --- | --- | --- | --- | --- |
| 1 | 4-{3-[4-(4-fluorophenyl)-1H-pyrazol-5-yl]piperidin-1-yl}-7H-pyrrolo[2,3-d]pyrimidine | −10.14 | −1.96 | −3.32 | −42.7 |
| 2 | 6-{3-[4-(4-fluorophenyl)-1H-pyrazol-5-yl]piperidin-1-yl}-9H-purine | −10.68 | −1.96 | −2.81 | −40.17 |

Example 3

Antitrypanosomal Assay

Six trypanosome species namely *T. b. brucei* (Tbb) GuTat3.1, *T. b. rhodesiense* (Tbr) IL1501, *T. b. gambiense* (Tbg) IL1922, *T. evansi* (Tev) Tansui, *T. equiperdum* (Teq) IVM-t1 and *T. congolense* (Tc) IL3000 were cultivated using HMI-9 medium and used in the study. Following the procedures reported in Suganuma et al. (2014): "Establishment of ATP-based luciferase viability assay in 96-well plate for

*Trypanosoma* congolense", *J Vet Med Sci* 76, 1437-41, the trypanocidal activity of the two compounds discussed herein was assessed at 25 µg/ml or 0.25 JIM. Both compounds showed substantial trypanocidal activity at 25 µg/ml. The $IC_{50}$ of the compounds against six trypanosome species was determined using serial dilution in a 96-well plate (Optical bottom plate, ThermoFisher SCIENTIFIC, MA, USA). After three days, 25 µL of CellTiter-Glo Luminescent cell viability reagent (Promega Corporation, WI, USA) was aliquoted into each well and luminosity was measured with a GloMax plate reader (Promega Corporation, WI, USA).

At first, the compounds were assayed at high and low concentrations of 0.25 or 25 µg/ml, respectively (Table 3). The compounds showed a broad-spectrum and strong inhibition of trypanosomal growth. At 25 µg/ml, the compounds suppressed all the test strains. TcIL3000, TbbGUTat3.1, TbrIL1501, TbgIL1922, Tev Tansui and Teq IVM-t1 showed more than 98% inhibition rate (Table 3) for both compounds. At a low concentration of 0.25 µg/ml, the inhibition rate was in the range between 1.82-15.94%.

TABLE 3

The inhibition rate of the compounds at 0.25 or 25 µg/ml against 6 *Trypanosoma* species, TcIL3000, TbbGUTat3.1, TbrIL1501, TbgIL1922, Tev Tansui and Teq IVM-t1.

| Trypanosome concentration | Compound 1 Inhibition rate | | Compound 2 Inhibition rate | |
|---|---|---|---|---|
| | 25 µg/ml | 0.25 µg/ml | 25 µg/ml | 0.25 µg/ml |
| TcIL3000 | 98.64 ± 0.16 | 8.85 ± 9.99 | 98.01 ± 0.2 | 8.085 ± 6.96 |
| TbbGUTat3.1 | 99.38 ± 0.02 | 13.18 ± 4.07 | 99.03 ± 0.02 | 13.88 ± 3.11 |
| TbrIL1501 | 99.34 ± 0.01 | 15.94 ± 11.11 | 98.64 ± 0.02 | 11.34 ± 6.63 |
| TbgIL1922 | 99.01 ± 0.01 | 2.82 ± 3.98 | 98.21 ± 0.02 | 1.82 ± 1.45 |
| Tev Tansui | 99.1 ± 0.46 | 9.14 ± 6.02 | 98.7 ± 0.04 | 6.14 ± 7.12 |
| Teq IVM-t1 | 99.22 ± 0.01 | 4.26 ± 6.01 | 98.62 ± 0.05 | 5.2 ± 4.11 |

*The values are represented as (mean ± SD)

Given the promising initial antitrypanosomal action of the compounds, the $IC_{50}$ was measured in the presence of several concentrations of the compound. Both compounds showed broad-spectrum antitrypanosomal action with $IC_{50}$ ranges of 2.65-13.33 µg/ml (Table 4). The strongest trypanocidal activity was found on TcIL3000 with $IC_{50}$=2.65±0.47 µg/ml, while the *T. evansi* showed the highest $IC_{50}$ value of 13.33±3.36 µg/ml.

TABLE 4

The $IC_{50}$ of the compounds against 6 *Trypanosoma* species, TcIL3000, TbbGUTat3.1, TbrIL1501, TbgIL1922, Tev Tansui and Teq IVM-t1

| Trypanosome | Compound 1 $IC_{50}$ (µg/ml)* | Compound 2 $IC_{50}$ (µg/ml)* |
|---|---|---|
| TcIL3000 | 2.65 ± 0.47 | 2.77 ± 0.57 |
| TbbGUTat3.1 | 3.53 ± 0.67 | 3.66 ± 0.77 |
| TbrIL1501 | 5.56 ± 0.13 | 4.65 ± 0.25 |
| TbgIL1922 | 3.51 ± 0.9 | 3.11 ± 0.88 |
| Tev Tansui | 13.33 ± 3.36 | 9.26 ± 1.2 |
| Teq IVM-t1 | 10.3 ± 0.36 | 9.12 ± 0.8 |

*The values are represented as (mean ± SD)

It is to be understood that the method of treating a protozoan infection described herein is not limited to the specific embodiments described above, but encompass any and all embodiments within the scope of the generic language of the following claims enabled by the embodiments described herein, or otherwise shown in the drawings or described above in terms sufficient to enable one of ordinary skill in the art to make and use the claimed subject matter.

I claim:

1. A method of treating a protozoan infection in a patient, comprising administering to a patient in need thereof a therapeutically effective amount of a pharmaceutical composition comprising an antiprotozoal compound and a pharmaceutically acceptable carrier, the antiprotozoal compound being selected from the group consisting of:

4-{3-[4-(4-fluorophenyl)-1H-pyrazol-5-yl]piperidin-1-yl}-7H-pyrrolo[2,3-d]pyrimidine having the formula:

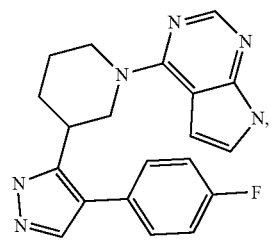

6-{13-[4-(4-fluorophenyl)-1H-pyrazol-5-yl]piperidin-1-yl}-9H-purine having the formula:

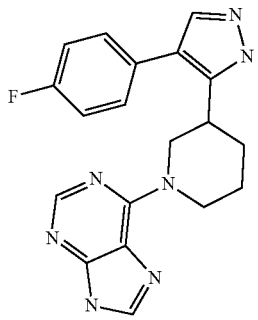 [SMILES: Fc1ccc(-c2cn[nH]c2C2CCCN(c3ncnc4[nH]cnc34)C2)cc1]

and a pharmaceutically acceptable salt, thereof,
wherein the protozoan is of a *Trypanosoma* genus.

2. The method of claim 1, wherein the protozoan is selected from the group consisting of *T. brucei, T. evansi, T. equiperdum*, and *T. congolense*.

3. The method of claim 2, wherein the protozoan is selected from the group consisting of *Trypanosoma brucei brucei* GUTat3.1, *T. b. rhodesiense* IL1501, *T. b. gambiense* IL1922, *T. evansi* Tansui, *T. equiperdum* IVM-t1, and *T. congolense* IL3000.

4. The method of claim 1, wherein the antiprotozoal compound is administered orally to the patient.

5. The method of claim 1, wherein the antiprotozoal compound is 4-{3-[4-(4-fluorophenyl)-1H-pyrazol-5-yl]piperidin-1-yl}-7H-pyrrolo[2,3-d]pyrimidine having the formula:

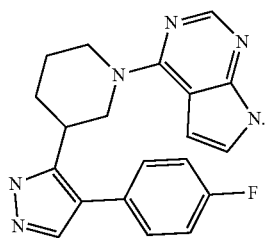
6. The method of claim 1, wherein the antiprotozoal compound is 6-{3-[4-(4-fluorophenyl)-1H-pyrazol-5-yl]piperidin-1-yl}-9H-purine having the formula:
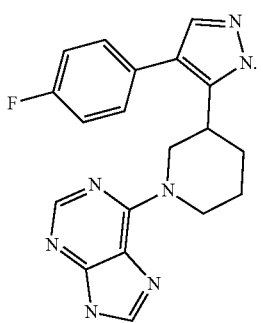
* * * * *